(12) United States Patent
Silver et al.

(10) Patent No.: US 10,488,277 B2
(45) Date of Patent: Nov. 26, 2019

(54) SYSTEMS AND METHODS FOR NON-INVASIVE MEASUREMENT OF MATERIAL MECHANICAL PROPERTIES AND INTERNAL BODY FORCES AND STRESSES

(71) Applicant: Rutgers, The State University of New Jersey, New Brunswick, NJ (US)

(72) Inventors: Frederick H. Silver, Mt. Bethel, PA (US); Dmitry Khavulya, Tabernacle, NJ (US); Mark Pierce, Jersey City, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/776,287

(22) PCT Filed: Oct. 12, 2016

(86) PCT No.: PCT/US2016/056588
§ 371 (c)(1),
(2) Date: May 15, 2018

(87) PCT Pub. No.: WO2017/087095
PCT Pub. Date: May 26, 2017

(65) Prior Publication Data
US 2018/0328798 A1 Nov. 15, 2018

Related U.S. Application Data

(60) Provisional application No. 62/256,214, filed on Nov. 17, 2015.

(51) Int. Cl.
*G01L 1/00* (2006.01)
*G01L 1/10* (2006.01)
(Continued)

(52) U.S. Cl.
CPC ............... *G01L 1/103* (2013.01); *A61B 5/00* (2013.01); *A61B 5/0051* (2013.01);
(Continued)

(58) Field of Classification Search
CPC .. G01L 1/103; G01L 5/06; A61B 5/00; A61B 5/0051; A61B 5/0066; G01N 3/32;
(Continued)

(56) References Cited

U.S. PATENT DOCUMENTS 4,418,573 A 12/1983 Madigosky et al.
4,777,599 A * 10/1988 Dorogi ................. A61B 5/0051
600/552

(Continued)

FOREIGN PATENT DOCUMENTS

GB 2029018 A 3/1980
JP S61118644 A 6/1986

OTHER PUBLICATIONS

Riede, Tobias: "Elasticity and Stress Relaxation of Rhesus Monkey (Macaca Mulatta) Vocal Folds", The Journal of Experimental Biology, Aug. 13, 2010, vol. 213, No. 17, pp. 2924-2932.

*Primary Examiner* — Max H Noori
(74) *Attorney, Agent, or Firm* — Fox Rothschild LLP

(57) ABSTRACT

Systems and methods for determining a Material's ("MTL") mechanical properties. The methods comprise: coupling a first end of MTL to a First Mechanical Mechanism ("FMM") movable in a First Direction ("FD") and coupling a second end of MTL to a Second Mechanical Mechanism ("SMM") movable in a Second Direction ("SD"); applying a first Pulling Force ("PF") to MTL; applying an Oscillating Force ("OF") to MTL; applying a second PF to MTL so as to cause any undulations in MTL to be removed and to cause a loading of fibers or polymeric units that support MTL; allowing MTL to oscillate through a series of cycles of
(Continued)

loading and unloading; measuring a strain/stress on MTL as a function of time; determining a natural frequency of MTL based on the strain/stress; and determining an elastic modulus of MTL using the natural frequency.

20 Claims, 8 Drawing Sheets

(51) Int. Cl.
    *A61B 5/00*     (2006.01)
    *G01L 5/06*     (2006.01)
    *G01N 3/32*     (2006.01)
    *G01L 5/00*     (2006.01)

(52) U.S. Cl.
    CPC .............. *A61B 5/0066* (2013.01); *G01L 5/06* (2013.01); *G01N 3/32* (2013.01); *G01N 2203/0075* (2013.01); *G01N 2203/0089* (2013.01); *G01N 2203/0094* (2013.01); *G01N 2203/0278* (2013.01); *G01N 2203/0647* (2013.01)

(58) Field of Classification Search
    CPC ... G01N 2203/0075; G01N 2203/0089; G01N 2203/0094; G01N 2203/0278; G01N 2203/0647
    USPC .......................................................... 73/788
    See application file for complete search history.

(56) References Cited

U.S. PATENT DOCUMENTS

| | | | |
|---|---|---|---|
| 5,474,070 A * | 12/1995 | Ophir | A61B 5/0048 |
| | | | 600/437 |
| 8,305,076 B2 * | 11/2012 | Sack | A61B 5/055 |
| | | | 324/309 |
| 8,965,487 B2 * | 2/2015 | Bouma | A61B 5/0059 |
| | | | 600/476 |
| 2003/0188585 A1 | 10/2003 | Esser et al. | |
| 2005/0267695 A1 * | 12/2005 | German | G01N 3/30 |
| | | | 702/41 |
| 2010/0057381 A1 | 3/2010 | Pardoen et al. | |
| 2010/0210971 A1 * | 8/2010 | Shabram | G01N 3/08 |
| | | | 600/587 |
| 2011/0041617 A1 * | 2/2011 | Cotrell | G01M 7/025 |
| | | | 73/660 |
| 2015/0038879 A1 | 2/2015 | Peipsi | |
| 2019/0003941 A1 * | 1/2019 | Wikswo | G02B 21/0004 |

* cited by examiner

SYSTEMS AND METHODS FOR NON-INVASIVE MEASUREMENT OF MATERIAL MECHANICAL PROPERTIES AND INTERNAL BODY FORCES AND STRESSES

CROSS REFERENCE TO RELATED APPLICATIONS

The present application claims priority to U.S. Provisional Patent Application Ser. No. 62/256,214 filed on Nov. 17, 2015, the entirety of which is hereby incorporated by reference for all purposes.

FIELD

This document relates generally to non-invasive techniques for measuring material mechanical properties and internal body forces and stresses.

BACKGROUND

As body mass increases during development, the body adapts to external mechanical loading by increasing the size of the functional units through a process termed mechanochemical transduction. Under normal physiological conditions, tissues found in mammals (such as the eye, blood vessels, lungs and skin) are under tension or residual stress. A dynamic loading pattern that stimulates mechanochemical transduction through the phosphorelay pathways is set up by tension at the tissue-cellular interface. The phosphorelay pathways control cell replication and protein synthesis in mammals. A number of studies have shown that changes in the mechanical properties of tissues accompany the onset and progression of several diseases (e.g., atherosclerosis, cirrhosis, glaucoma, and cancer).

Conventional Methods Used to Measure Mechanical Forces in Tissues

A number of methods have been used to study the mechanical properties of tissues. These methods include constant rate-of-strain, stress-relaxation, dynamic cyclic loading and other techniques many of which permanently destroy the tissue. In general, soft tissues or non-mineralized Extra-Cellular Matrices ("ECMs") (such as arterial wall, skin and tendon) have moduli between 1 and 2500 MPa. These values depend on the collagen orientation, collagen content, donor age, donor species and anatomical location from which samples are derived. In addition, Poisson's ratio (a parameter used in calculating the modulus in many of the studies using non-invasive techniques) is reported to vary from 0.125 for nucleus pulposis to 1.87 for the surface zone of human patellar cartilage.

Techniques such ultrasonography, elastography and vibrational analysis can be used without destroying the subject tissue. The results of these techniques produce results that do not match the results obtained with destructive techniques. Several studies have reported a value of the elastic modulus of about 20 kPa, which is much lower than is recognized in the scientific literature for ECMs.

Results of other studies have yielded important information concerning the stress-strain behaviors of tissues under different loading conditions. However, technical considerations (such as using a value of about 0.5 for Poisson's ratio) have resulted in values for the modulus that are dramatically different than the values reported using destructive techniques.

Problems exist which are associated with: (1) permanently damaging materials and tissues that are being tested; (2) use of values for mechanical parameters that are difficult to simulate accurately; and (3) difficulty properly interpreting the results of non-invasive methods. These problems lead to the need to develop new methods for analyzing the properties of materials and tissues.

Non-Invasive Studies Involving the Use of Acoustic Mechanical Waves

U.S. Pat. No. 4,646,754 to Seale ("the '754 patent") describes a non-invasive system for inducing vibrations in a selected element of the human body and detecting the nature of the responses for determining mechanical characteristics. The method described develops a mathematical model of the structure using adjustable parameters to make a fit of the data. The use of adjustable parameters in this approach is of concern.

Non-patent literature entitled "Vibrational Analysis Of Tendon, Mechanical Properties" written by Revel et al. ("Revel") describes the use of a small hammer and a laser vibrometer to measure the vibrational velocity of an Achilles tendon during uniaxial tensile testing. This document reports a first resonant frequency of 47 to about 57 Hz for stress levels up to about 7 MPa. A conclusion is made in the document that the first resonant frequency is a valued parameter for measurement of some physiological characteristics of tendon. However, the resonant frequencies appear to be very low for tendon considering the modulus of Achilles tendon is expected to be high.

U.S. Pat. No. 7,731,661 to Salcudean et al. ("the '661 patent") describes a method for applying a vibration signal to a region of tissue, measuring a response to a vibration at a plurality of locations and providing a model of the localized properties of a region of interest. The use of a poorly described model to interpret the results makes this approach less than useful.

U.S. Pat. No. 7,744,535 to Vanderby et al. ("the '535 patent") describes an ultrasound system for measuring strain subject to varying tension. The ultrasound system implements a process that calculates the strain and stiffness from the time of flight of the sound. However, the time of flight is dependent on the tissue density and modulus, which can only be estimated using this method.

U.S. Pat. No. 7,753,847 to Greenleaf et al. ("the '847 patent") describes a method for measuring mechanical properties of a subject. Such measurement is achieved by: applying ultrasonic vibration pulses in an on-off time sequence; measuring characteristics of detected harmonic signals; and calculating the mechanical properties using the measured characteristics. This document reports an elasticity of 20 kPa for cirrhosis of the liver. This 20 kPa value is only a fraction of that reported for collagenous tissues and seems rather low.

U.S. Pat. No. 7,946,180 to Sumi ("the '180 patent") shows an apparatus for storage of one strain tensor, strain-rate data, and pulse wave velocity vector data so that an elastic constant can be calculated. Again the calculations in this approach require modeling that may lead to large errors in the mechanical properties.

U.S. Pat. No. 8,167,804 to Kim et al. ("the '804 patent") discloses a method for monitoring vascular wall compliance by measuring the pulse wave velocity, the intramural strain and pulse wave velocity. This technique uses an assumed Poisson's ratio of 0.5 to calculate mechanical parameters. The use of an assumed Poisson's ratio is a problem in this approach.

U.S. Pat. No. 8,323,199 to Salcudean et al. ("the '199 patent") discloses an apparatus for imaging mechanical properties of a tissue region from within an endocavity. Images are collected after a probe is inserted in a cavity and the probe is vibrated using ultrasound. It is unclear in the '199 patent how the images are translated into mechanical properties using this method.

U.S. Patent Publication No. 2014/005548 to Douglas et al. ("the '548 patent publication") describes an ultrasonic diagnostic imaging system for shear wave analysis using an ultrasonic array probe having a 2-D array of transducer elements. The stiffness is measured by tracking the shear wave front over time. It is unclear how modulus values obtained using this technique compare to the values reported in the literature.

U.S. Patent Publication No. 2014/0081138 to Bercoff et al. ("the '138 patent publication") discloses a method for measuring a mean viscoelastic value of a soft material using a single probe with at least one transducer. The mean value is estimated by: inducing a constraint zone; measuring a displacement of the zone and of a zone away from the constraint zone; and determining a mean viscoelasticity of tissue displacement between the zones. It is unclear how the viscoelastic parameters measured using this approach compare with values reported in the literature Non-patent literature entitled "A Review Of Optical Coherence Elastography: Fundamentals, Techniques And Prospects" written by Kennedy et al. ("Kennedy") reviews Optical Coherence Elastography ("OCE") as a means to estimate the mechanical properties of tissues. In this document, assumptions are used that are inherent to analyzing acoustic vibrational data using similar techniques. The assumptions used in the studies reviewed include: (1) that a tissue is a linear solid with isotropic properties; (2) that measurement of the resulting displacement from loading with an acoustical wave can be used to estimate a mechanical property; (3) that viscoelastic considerations may not significantly affect the use of classical derivations of constitutive relationships between stress and strain; and (4) that the assumption of incompressibility (Poisson's ratio of about 0.5) will not cause significant calculation errors. The assumption that viscoelastic considerations do not affect the relationship between stress and strain does not agree with the literature results that the viscous contribution to the behavior of tissues such as skin can be as high as 50%.

U.S. Pat. No. 9,043,156 to Gallippi et al. ("the '156 patent") describes a method for determining the mechanical property parameter of sample by applying acoustic energy. The resulting mechanical property parameter requires the measurement of a response to acoustic energy application and the recovery response, as well as a determination of an additional mechanical parameter based on mathematical relationship between three (3) mechanical parameters. The limitation of this method is that it requires three (3) separate measurements and the result is an estimated elastic modulus.

SUMMARY

The present disclosure concerns systems and methods for non-invasive and non-destructive determinations of mechanical properties of a material. The material includes, but is not limited to, a material used in a commercial process, a material used in a laboratory process, a tissue in a living animal, or a tissue removed from a living animal.

The methods comprise: coupling a first end of the material to a first mechanical mechanism which is movable in a first direction and coupling a second end of the material to a second mechanical mechanism which is movable in a second direction opposed to the first direction; applying a first pulling force to the material by moving the first and second mechanical mechanisms a first distance in respective first and second directions; applying an oscillating force to the material having the first pulling force applied thereto (e.g., by an oscillating force generator); applying a second pulling force to the material by moving the first and second mechanical mechanism a second distance in respective first and second directions, where the second pulling force causes any undulations in the material to be removed and causes a loading of fibers or polymeric units that support the material; allowing the material to oscillate through a series of cycles of loading and unloading (e.g., at frequencies between 10-2000 Hz); measuring a strain or stress on the material as a function of time while the material oscillates; determining a natural frequency of the material based on the strain or stress previously measured; and determining an elastic modulus of the material using the natural frequency.

In some scenarios, the oscillating force is applied to the material by an electrical, magnetic, mechanical, electromechanical or vibrating element. This element is also referred to herein as an oscillating force generator. The oscillating force generator can be selected from the group consisting of a vibrating hammer, an oscillating hydraulic device, an oscillating acoustic device, an oscillating magnetic field generator, an oscillating electrical field generator, an oscillating electromagnetic field generator, and an oscillating piezoelectric crystal. The oscillating force can comprise an oscillating acoustic force. A tension of the material can range from zero Newton (0 N) to five hundred Newton (500 N) when the oscillating force is being applied thereto.

In those or other scenarios, the elastic modulus is determined using the following Mathematical Equation $$E = (2\pi f_n m)^2 \left(\frac{L}{A}\right)$$

where E represents a modulus, $f_n$ is the natural vibration frequency, m represents a mass of the sample material, L represents a length of the sample material, and A represents the cross-sectional area of the sample material. The elastic modulus is obtained by multiplying the modulus E by an elastic fraction measured separately on the material from incremental stress-strain curves.

In those or other scenarios, a viscoelasticity of the material may additionally or alternatively be measured when the oscillating force is being applied to the material. A first diagnosis is transformed into a more precise second diagnosis based on the elastic modulus and/or the viscoelasticity.

DESCRIPTION OF THE DRAWINGS

The present solution will be described with reference to the following drawing figures, in which like numerals represent like items throughout the figures.

DETAILED DESCRIPTION

Figure 1:
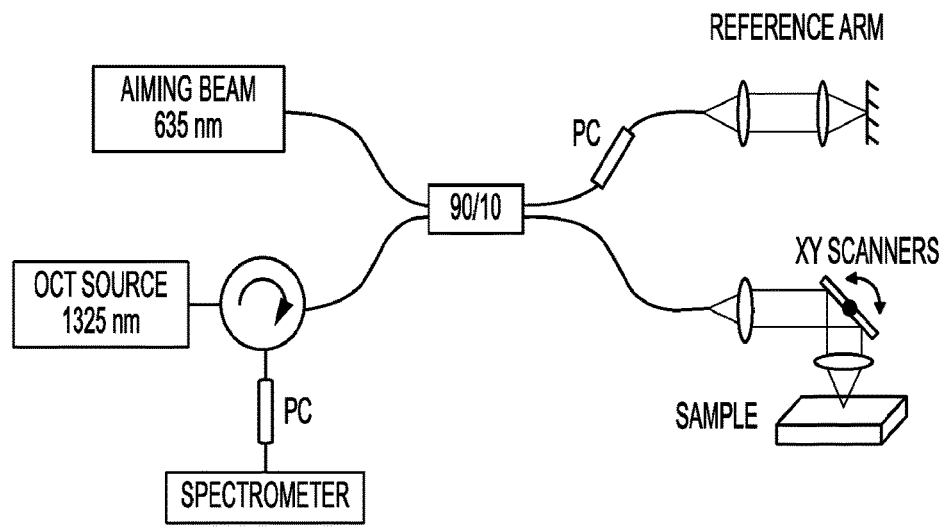
FIG. 1 is a schematic illustration of components of an OCT system used to measure the natural frequency of a material loaded using a vibrational stimulus.

It will be readily understood that the components of the present solution as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the present solution are presented in drawings, the drawings are not necessarily drawn to scale unless specifically indicated.

The present solution may be embodied in other specific forms without departing from its spirit or essential characteristics. The described embodiments are to be considered in all respects only as illustrative and not restrictive. The scope of the present solution is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the present solution. Rather, language referring to the features and advantages is understood to mean that a specific feature, advantage, or characteristic described in connection with an embodiment is included in at least one embodiment of the present solution. Thus, discussions of the features and advantages, and similar language, throughout the specification may, but do not necessarily, refer to the same embodiment.

Furthermore, the described features, advantages and characteristics of the present solution may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the present solution.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

The change of tissue mechanical properties (e.g., elastic modulus or stiffness) has been linked to pathogenesis of many diseases (including fibrosis and cancer). For example, tumors are much harder than healthy tissues. This change in the stiffness is routinely examined by physicians through palpation. Sensitive techniques and methods, that can be used to non-invasively determine the mechanical property of tissue in patients, can lead to early diagnosis and treatment.

The present disclosure concerns systems and methods for non-invasive and non-destructive determinations of mechanical properties in living patients. The mechanical properties include, but are not limited to, strain, elastic modulus and/or viscoelasticity. The determination is made by measuring the natural frequency of a tissue or material under tension. The non-invasive measurement improves the ability of clinicians to provide early diagnosis of highly prevalent conditions (e.g., cancer, fibrosis or other conditions associated with tissue stiffness).

The present technique for non-invasive measurement of mechanical forces in tissues yields values found using destructive techniques. In some scenarios, the mechanical forces acting on a tissue are measured by determining the strain on the tissue and modulus of the material using vibrational analysis. In other scenarios, (a) the modulus of a tissue is measured using vibrational analysis on a tissue and/or (b) the viscoelasticity of a tissue is measured by determining the in-phase (elastic) and out-of-phase (viscous) response when an external vibration is applied.

An oscillating mechanical load applied to tissue or other materials can be used to estimate the mechanical properties of these materials. The limitations of this oscillation based technique include the assumptions that material is linearly elastic, the material is incompressible, and the mechanical property (such as modulus) can be calculated from the displacement measurements made within the tissue. The assumption of linear elasticity and incompressibility are well known to have severe limitations since Poisson's ratios for tissue have been shown to vary significantly from a half (0.5). In addition, tissues are viscoelastic, and therefore the properties are time-dependent. The easiest way to separate out the elastic and viscous components in the viscoelastic response is to make measurements at zero (0) time and after relaxation has occurred. By assuming linearity, incompressibility and elasticity, the calculated value of mechanical properties (such as the modulus) have significant errors introduced.

What is needed is a simple experimental method and device to determine the elastic modulus of tissue after introducing an oscillating mechanical vibration. While it is necessary to assume linearity between stress and strain to use standard mathematical relationships, it is possible to apply these equations under conditions where linearity between elastic stress and strain is a good approximation for collagenous materials.

Exemplary Systems and Methods for Non-Invasive and Non-Destructive Determinations of Mechanical Properties in Living Patients As noted above, the present disclosure concerns systems and methods in which an oscillating mechanical vibration is applied to a tissue and the natural frequency of the resulting vibrations that occurs as a result of the externally applied load is measured. For a linearly elastic material, the relationship between the natural frequency and vibrational modulus is given by Mathematical Equation (1).

$$E = (2\pi f_n m)^2 \left(\frac{L}{A}\right) \quad (1)$$

where E represents a modulus, $f_n$ is the natural vibration frequency, m represents a mass of the sample material, L represents a length of the sample material, and A represents the cross-sectional area of the sample material.

Mathematical Equation (1) states that the elastic modulus for a linear elastic material is related to the natural frequency squared of the resulting vibrations multiplied by the mass squared times the length divided by the cross-sectional area. By measuring the natural frequency of a material that is vibrated assuming that it behaves in a linear elastic manner, the modulus can be obtained using Mathematical Equation (1). Although collagen and ECMs are viscoelastic, they behave quasi-elastically at high strains, i.e., the stress and strain appear linear. In addition, the elastic part of the modulus can be obtained by measuring the stress at equilibrium and correcting the modulus by the elastic fraction, i.e., the fraction of energy stored elastically. Thus, by measuring the natural frequency that arises from an externally applied vibrational force and correcting for the elastic fraction, the elastic modulus can be obtained from Mathematical Equation (1). Alternately, the modulus of a viscoelastic tissue can be obtained from Mathematical Equation (1) from the natural frequency by applying an external oscillation to an ECM that has been stretched into the linear region of the stress-strain curve. As is known, the elastic stress for collagen is approximately linear with strain and is strain-rate independent for strain-rates up to one thousand percent per second (1000%/sec). The viscous contribution to the stress is known to increase with strain-rate for collagen. This pertains to ECMs rich in the fibrillar collagens. This means the elastic modulus can be calculated from the modulus obtained from Mathematical Equation (1) after correction by the elastic fraction. In addition, the viscous contribution to the modulus can also be obtained from the difference between the total modulus calculated from the Mathematical Equation (1) times one (1) minus the elastic fraction. In addition, the decay time for a viscoelastic material is obtained from the time it takes the applied oscillating stress to decay to an equilibrium value. In this manner, the viscoelastic properties of a material can be obtained from the resonant frequency of a material that is oscillated using sinusoidal forces as described above.

In those or other scenarios, the force is applied to the material by a vibrating hammer, an oscillating hydraulic device, an oscillating acoustic device, an oscillating magnetic field generator, an oscillating electrical field generator, an oscillating electromagnetic field generator, an oscillating piezoelectric crystal, and/or any other electrical, magnetic and/or mechanical mechanisms that applies a varying force over time. Each of the listed electrical, magnetic and/or mechanical mechanisms for applying forces to the material (e.g., tissue sample 208 of FIG. 2) are well known in the art, and therefore will not be described herein. Any known or to be known electrical, magnetic and/or mechanical mechanism can be used herein without limitation.

In those or other scenarios, an oscillating acoustic force is applied to a material or wet tissue that is stretched so that the tension ranges from zero Newton (0 N) to five hundred Newton (500 N). The sample is allowed to oscillate through a series of cycles of loading and unloading at frequencies between ten Hertz (10 Hz) and two thousand Hertz (2000 Hz). Then, the oscillating acoustic force is removed from the sample. The sample is stretched to remove any undulations in it as well as to load the fibers or polymeric units that support the sample. Previous observations on tissues using elastography have resulted in tissue moduli values in the KPa range whereas reports on moduli measured using uniaxial tensile tests reveal moduli for collagenous tissues in the MPa range. This is probably due to the need to pre-stretch the material to a strain where the tissue fibers are loaded in tension.

The strain or stress as a function of time is measured and the natural frequency is determined by obtaining the Fourier transform of the strain or stress in the frequency domain. Once the natural frequency is obtained from the Fourier transform of the strain or stress in the time domain, the elastic modulus is obtained by substitution into Mathematical Equation (1) presented above. The elastic modulus is obtained by multiplying the modulus obtained in Mathematical Equation (1) by the elastic fraction measured separately on the tissue from incremental stress-strain curves. The elastic fraction calibration curve is strain-rate dependent and is obtained from incremental stress-strain measurements on samples at different strain-rates.

Figure 12:
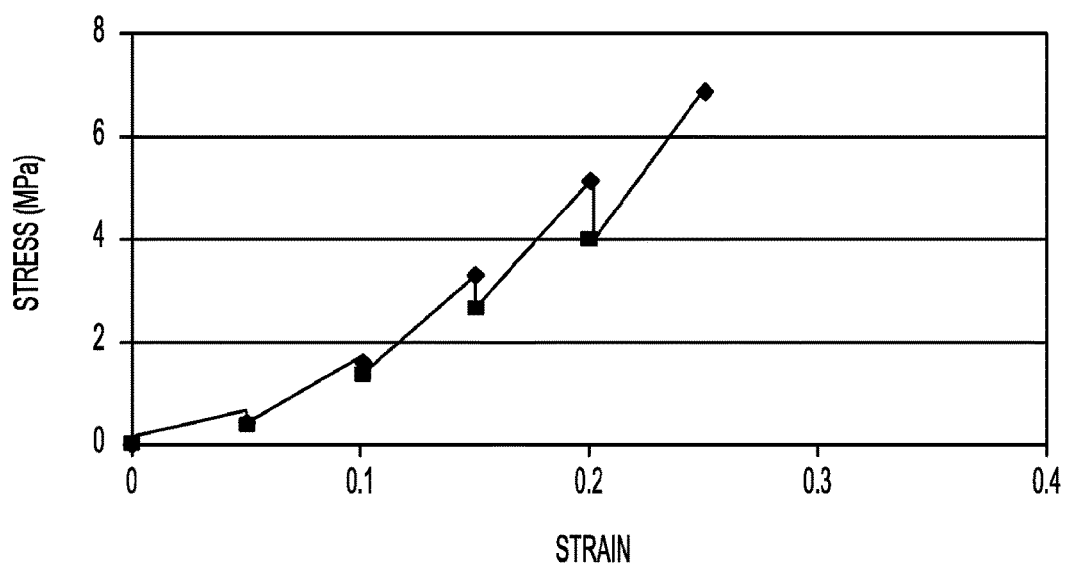
FIG. 12 provides an exemplary stress-strain curve.

In some scenarios, the elastic fraction is obtained by measuring the ratio of the instantaneous force or stress and dividing it by the equilibrium force or stress that occurs after the material has relaxed. FIG. 12 provides an incremental stress-strain curve for normal human articular cartilage. When a tissue is loaded in tension and a strain increments is added, the initial stress represents a combination of the elastic and viscous components. The stress then decays to an equilibrium value (lower point at a constant strain). The equilibrium value represents the elastic stress while the initial stress (top point at a constant) represents a combination of the elastic and viscous stress. Elastic and viscous stress-strain curves for "normal" articular cartilage are constructed by connecting all the top and bottom points. An exemplary stress-strain curve is shown in FIG. 12. The elastic component is independent of strain rate for fibrous ECMs. The elastic fraction is the ratio of the equilibrium stress to the initial stress. The elastic fraction of tendon is about seven tenths (0.7) while that of skin is five tenths (0.5) at strains of about five percent (5%) and the elastic fraction increased to seven tenths (0.7) at strains of about twenty percent (20%) or more.

The following EXAMPLES are provided in order to further illustrate the present solution. The scope of the present solution, however, is not to be considered limited in any way thereby.

EXAMPLE 1

In this example scenario, the modulus of materials was measured using tensile testing. Samples to be tested were prepared from strips of polymeric materials with dimensions two and a half centimeters (2.5 cm) wide, one millimeter (1 mm) thick and six and three tenths of a centimeter (6.3 cm) long weighing between one tenth of a gram (0.1 g) and one gram (1.0 g). The samples were placed in the grips of a micrometer connected to a force gauge and stretched until they were under a force of about half Newton (0.5 N). The samples were then stretched in strain increments of five hundredth of a percent (0.05%) and the force recorded. The stress strain curves were calculated from this data and a modulus was obtained from the slope of the stress-strain curve.

EXAMPLE 2

Figure 2:
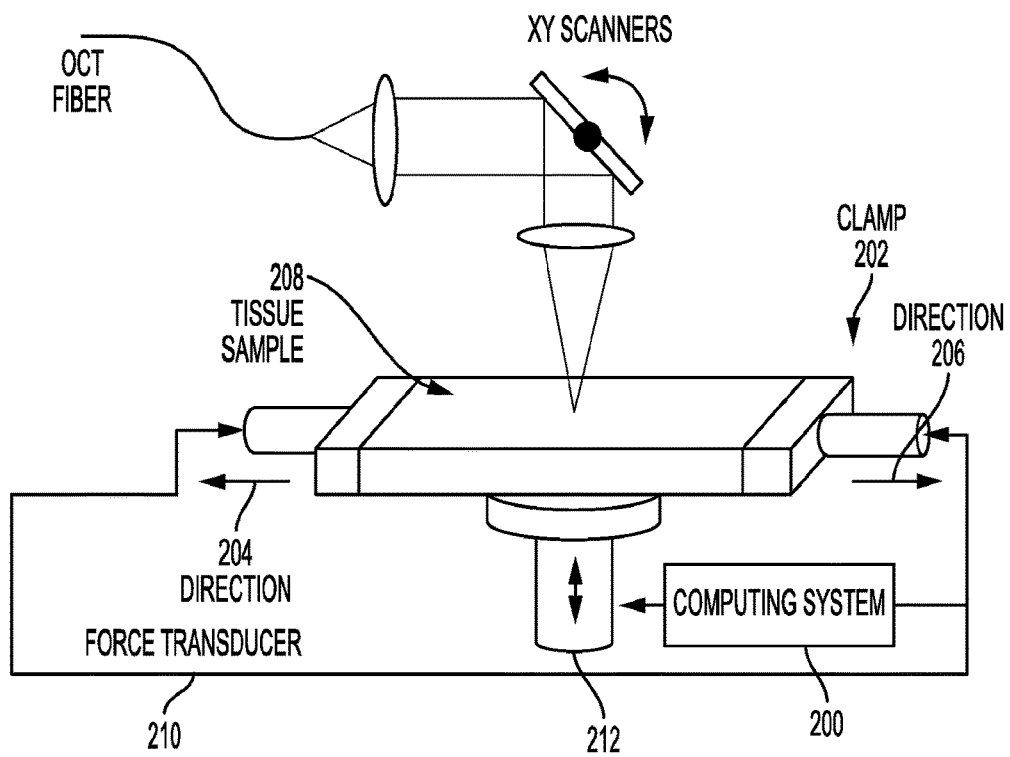
FIG. 2 is a schematic illustration showing an exemplary setup used in an experiment.
Figure 3:
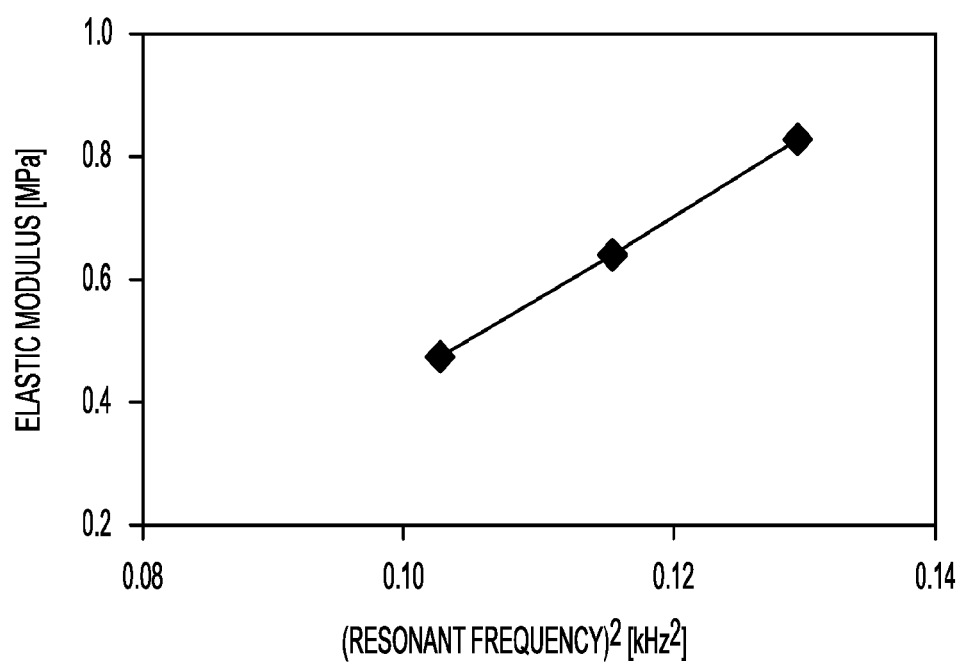
FIG. 3 is a graph showing the square of the natural frequency plotted versus the modulus measured using tensile testing.

In this example, the modulus was measured using vibrational analysis. The natural frequency was measured using an OCT system as shown in FIGS. 1-2. FIG. 3 shows the square of the natural frequency plotted versus the modulus measured using tensile testing as described in EXAMPLE 1. The vibrational stage of the OCT included a micrometer by which the sample was stretched to the same extent as was done in the uniaxial tensile tests. A speaker was mounted under the sample and vibrated the sample to acoustic frequencies between one hundred Hertz (100 Hz) and one thousand Hertz (1000 Hz). The natural frequency of the sample was obtained from the driving frequency that produced the largest displacement in the sample's resonant frequency. The value of the elastic modulus was calculated from Mathematical Equation (1).

EXAMPLE 3

In this scenario, the tensile and vibrational moduli for silicone rubber model materials were measured. The tensile E and vibrational Ev moduli of silicone elastomers were measured using the methods of EXAMPLES 1 and 2 described above. The silicone elastomeric base was mixed with curing agent at a 10:1 ratio and allowed to cure at twenty-five degrees Celsius (25° C.) overnight. A value of the resonant frequency of three hundred sixty (360) cycles per second was obtained for a sample that after use of Mathematical Equation (1) resulted in a value of Ev ninety-one hundredths of a Mega-Pascal (0.91 MPa). The value of E from the slope of the tensile measurements was found to be eight tenths of a Mega-Pascal (0.80 MPa).

EXAMPLE 4

In this scenario, the tensile and vibrational moduli for a rubber glove were measured. Samples of rubber obtained from a rubber glove were prepared and tested according to EXAMPLES 1 and 2. The value of the resonant frequency for the rubber glove was found to be one hundred twenty-seven (127) cycles per second. This translated into a value of Ev of sixty-four hundredths of a Mega-Pascal (0.64 MPa) using Mathematical Equation (1). The value of the tensile modulus was found to be eighth tenths (0.80) using uniaxial tensile tests.

EXAMPLE 5

In this scenario, the tensile and vibrational moduli for decellurized dermis were measured. Samples of decellularized dermis were obtained. The samples were stretched with the micrometer stage to about ten percent (10%) and tested to determine the moduli as described in EXAMPLES 1 and 2. The natural frequency obtained was six hundred sixty-three (663) cycles per second. This was equivalent to a modulus of four and ninety-three hundredths of a Mega-Pascal (4.93 MPa). The modulus obtained from uniaxial tensile tests was four Mega-Pascal (4.0 MPa).

Figure 4:
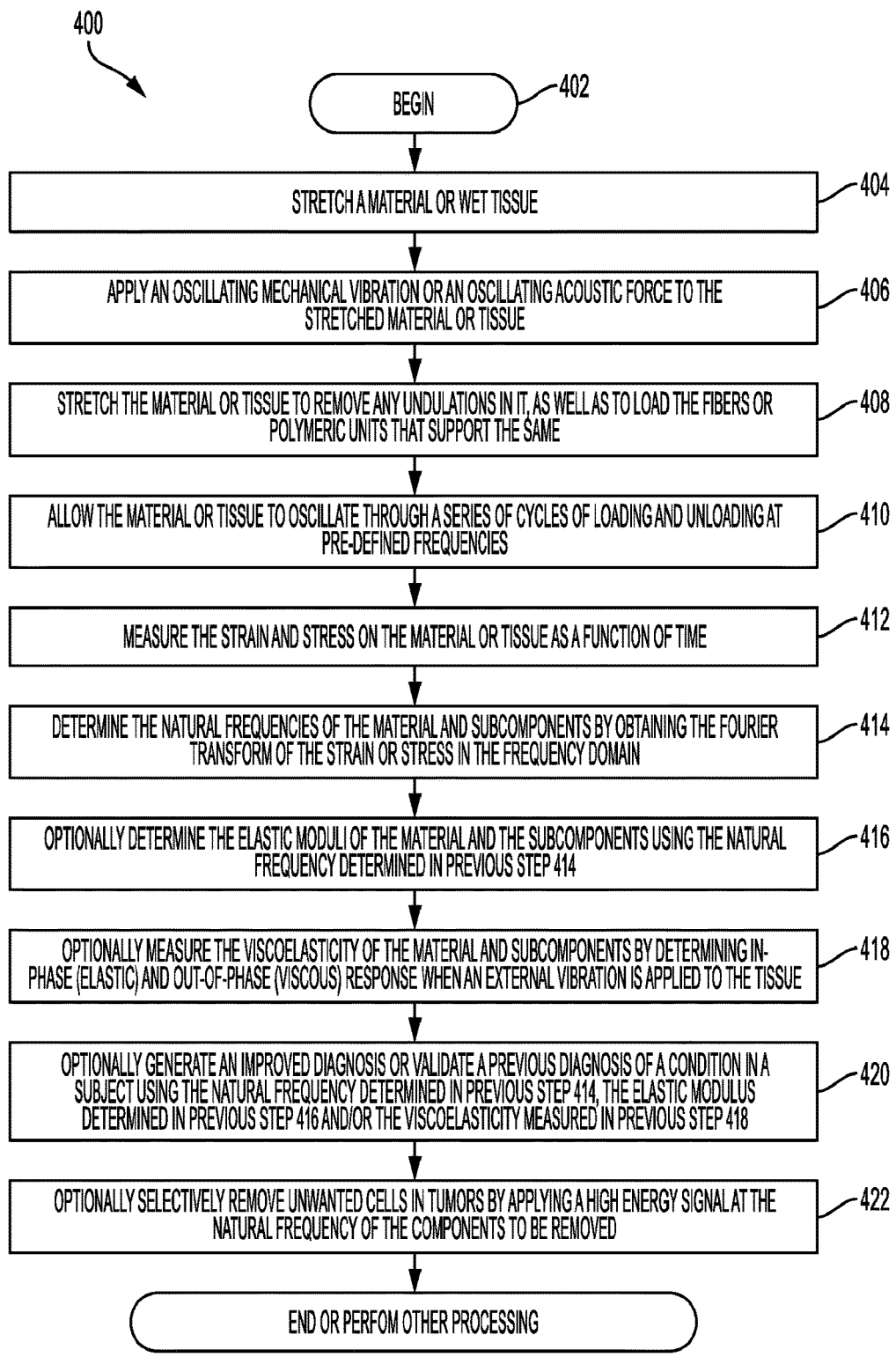
FIG. 4 is a flow diagram of an exemplary method for non-invasive and non-destructive determinations of mechanical properties in living patients.

Referring now to FIG. 4, there is provided a flow diagram of an exemplary method 400 for non-invasive and non-destructive determinations of mechanical properties of a material (e.g., an elastic and/or viscoelastic material). The material includes, but is not limited to, a material used in a commercial process/product (e.g., an airplane part), a material used in a laboratory process, a tissue in a living animal, or a tissue removed from a living animal.

Method 400 begins with step 402 and continues with step 404 where a material or wet tissue (e.g., tissue sample 208 of FIG. 2) is stretched (e.g., so that the tension ranges between 0 N to 500 N) at one or more ends thereof. In some scenarios, the material is already under tension. In other scenarios, clamps (e.g., clamps 202 of FIG. 1) are used to secure the tissue in an extended planar arrangement, such as that shown in FIG. 2. The clamps are moved in opposing directions (e.g., directions 204 and 206 of FIG. 1) which causes the tissue to be made longer without tearing or breaking. Movement of the clamps causes a pulling force to be applied to the material or wet tissue. Clamps are well known in the art, and therefore will not be described herein. Any known or to be known clamps can be used herein without limitation. Also, other mechanical securement mechanisms can be employed in addition to or as alternatives to the clamps. As should be understood, operations of the clamps and other mechanical securement mechanisms can be controlled by a controller, such as a computing system and/or driving mechanical device (e.g., a motor). Controllers, computing systems and mechanical devices are well known in the art, and therefore will not be described in detail herein. An exemplary computing system is discussed below in relation to FIG. 5.

Next in step 406, an oscillating mechanical vibration or an oscillating acoustic force is applied to the stretched material or tissue. In some scenarios, a force transducer (e.g., force transducer 210 of FIG. 2) is used to apply the oscillating mechanical vibration or oscillating acoustic force to the tissue. The force transducer can be arranged to move in two opposing directions (e.g., directions 212 of FIG. 2) which are both perpendicular to the directions (e.g., directions 204-206 of FIG. 2) in which the clamps are moved for purposes of stretching the tissue. As should be understood, operations of the force transducer can be controlled by a controller, such as a computing system. Controllers and computing systems are well known in the art, and therefore will not be described in detail herein. An exemplary computing system is discussed below in relation to FIG. 5. In other scenarios, the oscillating force is applied to the stretched material/tissue by an electrical, magnetic, mechanical, electromechanical or vibrating element. The electrical, magnetic, mechanical, electromechanical or vibrating element can include, but is not limited to, a vibrating hammer, an oscillating hydraulic device, an oscillating acoustic device, an oscillating magnetic field generator, an oscillating electrical field generator, an oscillating electromagnetic field generator, and/or an oscillating piezoelectric crystal.

In step 408, the material or tissue is further stretched to remove any undulations in it as well as to load the fibers or polymeric units that support the same. The material or tissue is then allowed to oscillate through a series of cycles of loading and unloading (e.g., between frequencies of 10 Hz to 2000 Hz), as shown by step 410. In some scenarios, the strain and stress on the material or tissue is then measured as a function of time, as shown by step 412.

The natural frequencies of the material and subcomponents are determined in step 414. This determination is achieved by obtaining the Fourier Transform of the strain and stress in the frequency domain. The strain provides a measurement for the vibrational modulus. The stress provides a measurement for the tensile modulus. A vibrational OTC measurement can be made to obtain the vibrational modulus.

Figure 6:
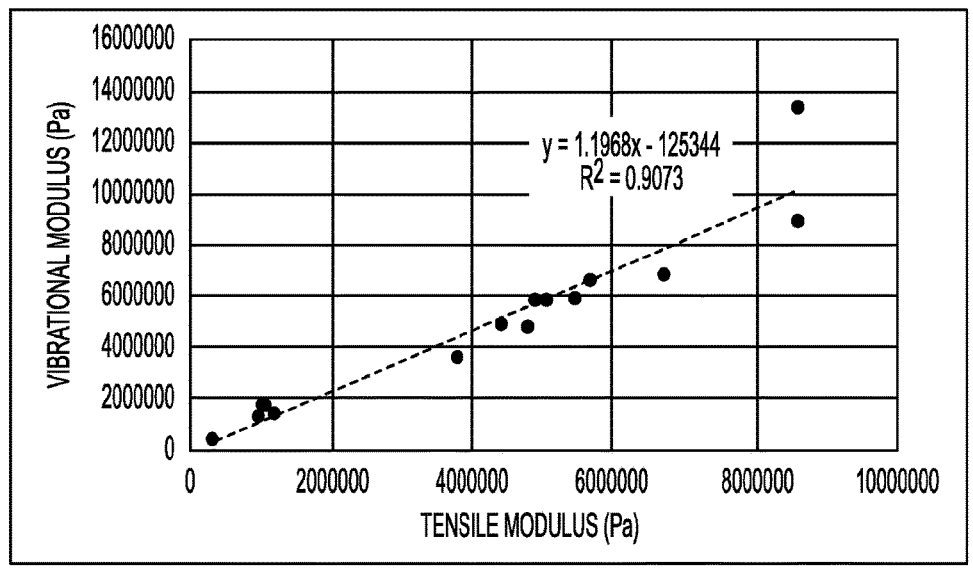
FIG. 6 shows an exemplary calibration curve of vibrational modulus from Mathematical Equation (1) provided below versus tensile modulus for silicone rubber and decellularized dermis, where the tensile was calculated from uniaxial incremental stress-strain curves.
Figure 7:
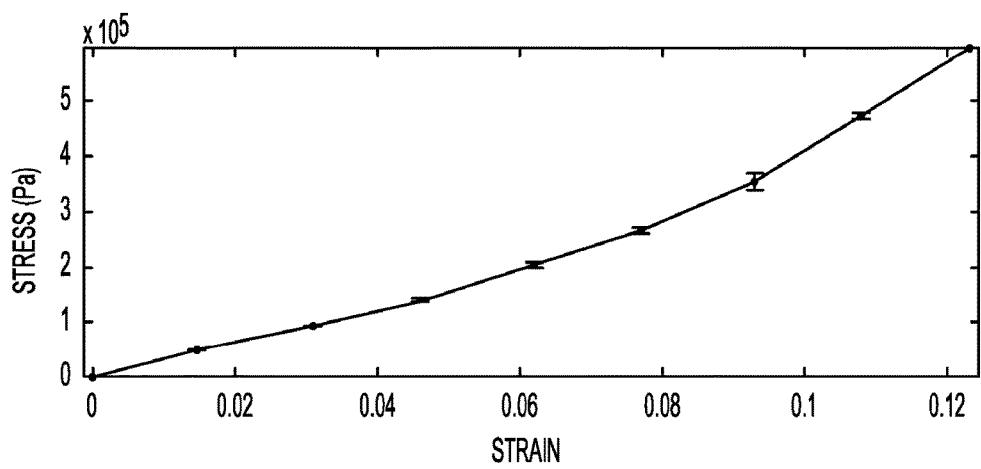
FIG. 7 shows an exemplary tensile stress-strain curve for decellularized dermis.
Figure 8:
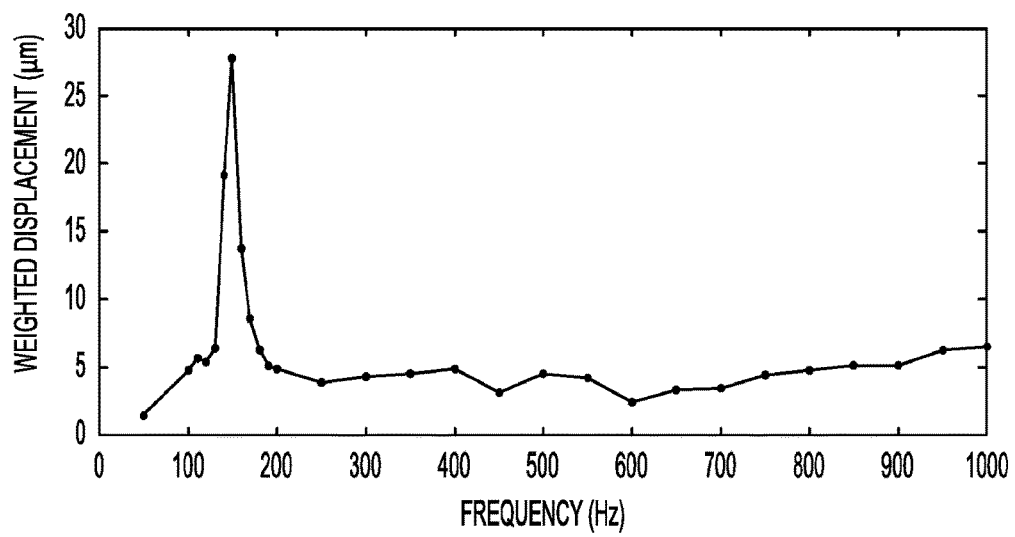
FIG. 8 shows an exemplary graph showing the natural frequency for a material composed of a single component (e.g., decellularized dermis) at a strain of five percent (5%).
Figure 9:
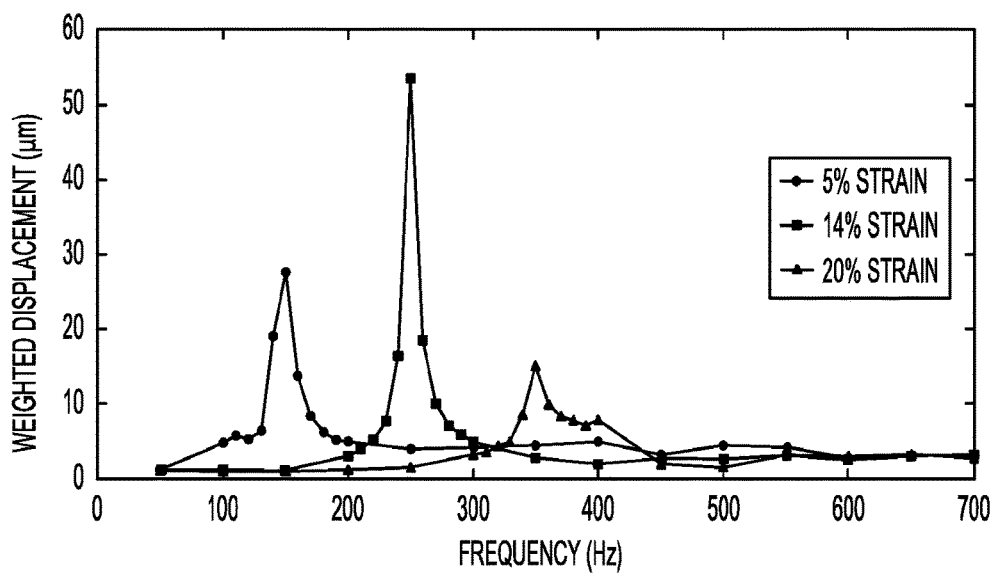
FIG. 9 provides an exemplary graph that shows the dependence of the natural frequency of the material on the strain.

An exemplary calibration curve of vibrational modulus from Mathematical Equation (1) versus tensile modulus is shown in FIG. 6 for silicone rubber and decellularized dermis, where the tensile modulus was calculated from uniaxial incremental stress-strain curves. An exemplary tensile stress-strain curve for decellularized dermis is shown in FIG. 7. An exemplary graph showing the natural frequency for a material composed of a single component (e.g., decellularized dermis) at a strain of five percent (5%) is provided in FIG. 8. An exemplary graph is provided in FIG. 9 that shows the dependence of the natural frequency of the material on the strain. The following TABLE 1 comprises a calibration table of natural frequency and tissue components.

TABLE 1

| Tissue Component | Strain | Natural Frequency |
|---|---|---|
| Dermis | | |
| Collagen Fibers | 5% | 150 |
| | 14% | 260 |
| | 20% | 350 |
| Cartilage | | |
| Collagen Fibers | 3% | About 150 |
| Bone | 3% | 900 |

Figure 10:
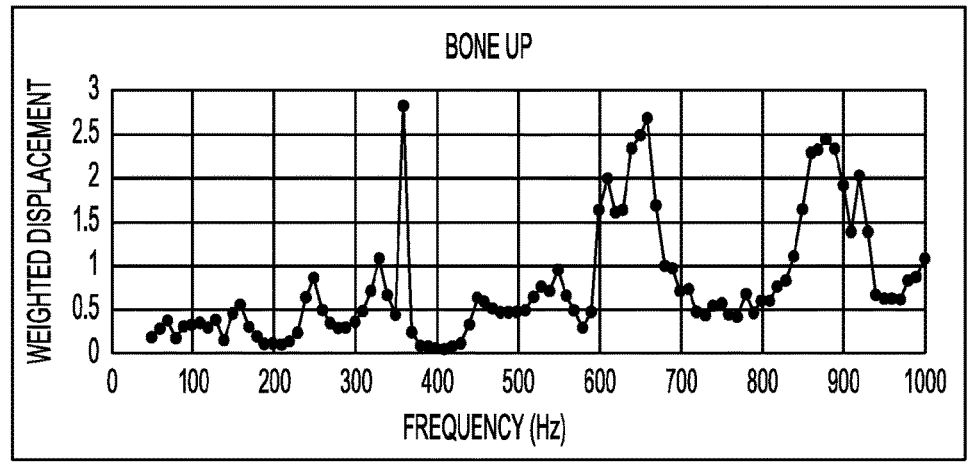
FIGS. 10 and 11 provide graphs that are useful for understanding how natural frequencies for a multicomponent material are determined.
Figure 11:
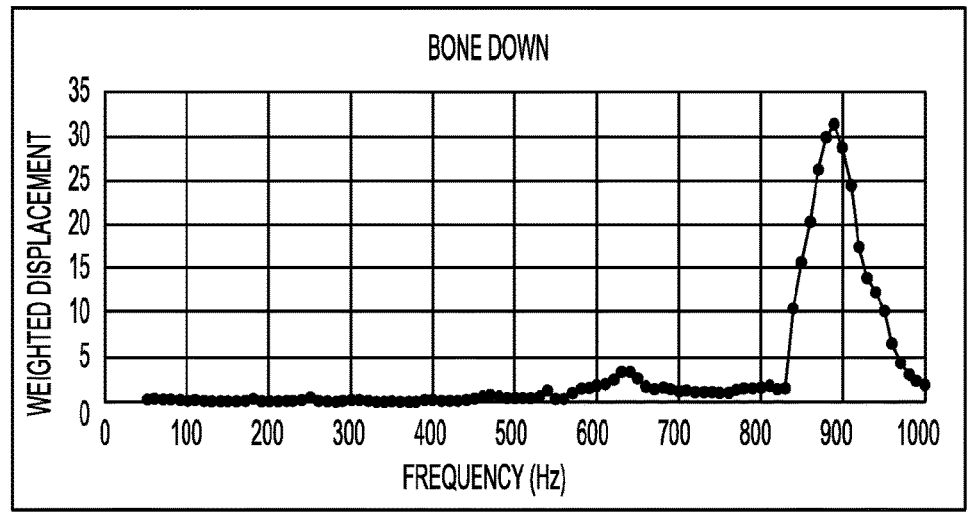

A typical determination of the natural frequencies of a multicomponent material (e.g., Bovine Articular Cartilage) is shown in FIGS. 10-11.

In some scenarios, the OTC measurement can be made via a handheld scanner. The handheld scanner implements all or a portion of method 400. The handheld scanner may include components for applying oscillating forces to the secured material and/or a computing device for determining a material's stress, strain, natural frequency, elastic modulus and/or viscoelasticity. An exemplary architecture for a computing device which can be contained in the handheld device is provided in FIG. 5. The present solution is not limited in this regard. Notably, in some handheld scanner scenarios the tissue does not need to be stretched at either end since most tissues are under tension.

The vibrational modulus can be determined using other techniques than the OTC based technique described herein. These other techniques include, but are not limited to, ultrasound, Magnetic Resonance Imaging ("MRI"), light microscopy, photography, and/or infrared photograph. In this case, the principle is the same: the modulus of a material can be determined by measuring the frequency that results in the maximum displacement of the material being vibrated. For instance, ultrasound works in the Mega-Hertz range. In method 400, the material is vibrated at a frequency between zero Hertz (0 Hz) and one thousand five hundred Hertz (1500 Hz). By combining the low frequency vibration (e.g., via a speaker) with the high frequency ultrasound imaging vibration (via an ultrasound transducer), the change in the material's dimension (or material's displacement) created by the low frequency vibration is measured via ultrasound imaging. The present solution is not limited to the particulars of this ultrasound example.

The elastic modulus of the material and subcomponents are optionally determined in step 416 using the natural frequency. In some scenarios, the elastic modulus is determined using Mathematical Equation (1) presented above. A modulus E is obtained by solving Mathematical Equation (1). The elastic modulus is obtained by multiplying the modulus E by an elastic fraction measured separately on the material from incremental stress-strain curves. The present solution is not limited to the techniques discussed herein for determining the elastic modulus. Other techniques can be used here without limitation.

The viscoelasticity of the material and subcomponents may optionally be measured as well as shown by step 418. The viscoelasticity is measured by determining in-phase (elastic) or out-of-phase (viscous) response when an external vibration is applied to the material. For example, in some scenarios, the viscous contribution to the elastic modulus is obtained from the difference between the total elastic modulus times one (1) minus the elastic fraction. Also, the decay time for the material is obtained from the time it takes the applied oscillating stress to decay to an equilibrium value.

The natural frequency, elastic modulus and/or viscoelasticity of the material and/or subcomponents is(are) then used in step 420 to optionally generate an improved diagnosis or validate a previous diagnosis of a subject's condition (e.g., cancer, fibrosis or other conditions associated with tissue stiffness). A diagnosis is improved here because the present technique provides a means to directly compute an elastic modulus (whereas in other conventional techniques a tangent to a curve needs to be derived which provides less accurate results especially for viscoelastic materials). The improved diagnosis can involve translating or transforming a first diagnosis into a more precise second diagnosis. For example, the first diagnosis is the existence of a tumor, and the more precise second diagnosis is a tumor that was malignant.

In some scenarios, the diagnosis is generated by the computing system using pre-stored Look Up Tables ("LUTs") of information correlating medical conditions with natural frequency, elastic modulus, and/or viscoelasticity values. An exemplary LUT is provided below as TABLE 2.

TABLE 2

| Condition | Change in Modulus With Respect to Values for Normal Tissues |
|---|---|
| Arteriosclerosis | Decreased |
| Cancerous Tumor | Increased |
| Fatty Liver | Decreased |
| Left Ventricular Hypertrophy | Decreased |
| Liver Fibrosis | Increased |
| Osteoarthritis | Decreased |
| Pulmonary Fibrosis | Increased |
| Scar Tissue | Increased |

Additionally or alternatively, various algorithms can be employed to compute a diagnosis value using the values determined for natural frequency, elastic modulus and/or viscoelasticity. For example, an amplitude of the signal can be used as a weighting factor for diagnosis purposes. In this case, the tissue behavior can be modeled by multiply the amplitude of the signal by the frequency, and calculating the overall tissue modulus. Let's assume that collagen of a first type vibrates at natural frequency $X_1$ and has an associated signal amplitude of $A_1$. Collagen of a second type vibrates at natural frequency $X_2$ and has an associated signal amplitude of $A_2$. The overall tissue's frequency behavior $T_{behavior}$ is then computed in accordance with the following Mathematical Equation.

$$T_{behavior} = A_1 X_1 + A_2 X_2$$

The value of $T_{behavior}$ is then used to generate a diagnosis value for a given subject. The present solution is not limited to the particulars of this example.

In some scenarios, method 400 continues with optional step 422. In step 422, unwanted cells or tissue in tumors are selectively removed by applying a high energy signal at the natural frequency of the components to be removed. For example, it is desirable to only remove cells from the material and not collagen. The cells have a natural frequency much lower than the collagen. Therefore, if the material is vibrated at the lower natural frequency, then the cells would be removed and not the collagen. The present solution is not limited in this regard. Upon completing one or more of steps 414-422, step 424 is performed where method 400 ends or other processing is performed.

Figure 5:
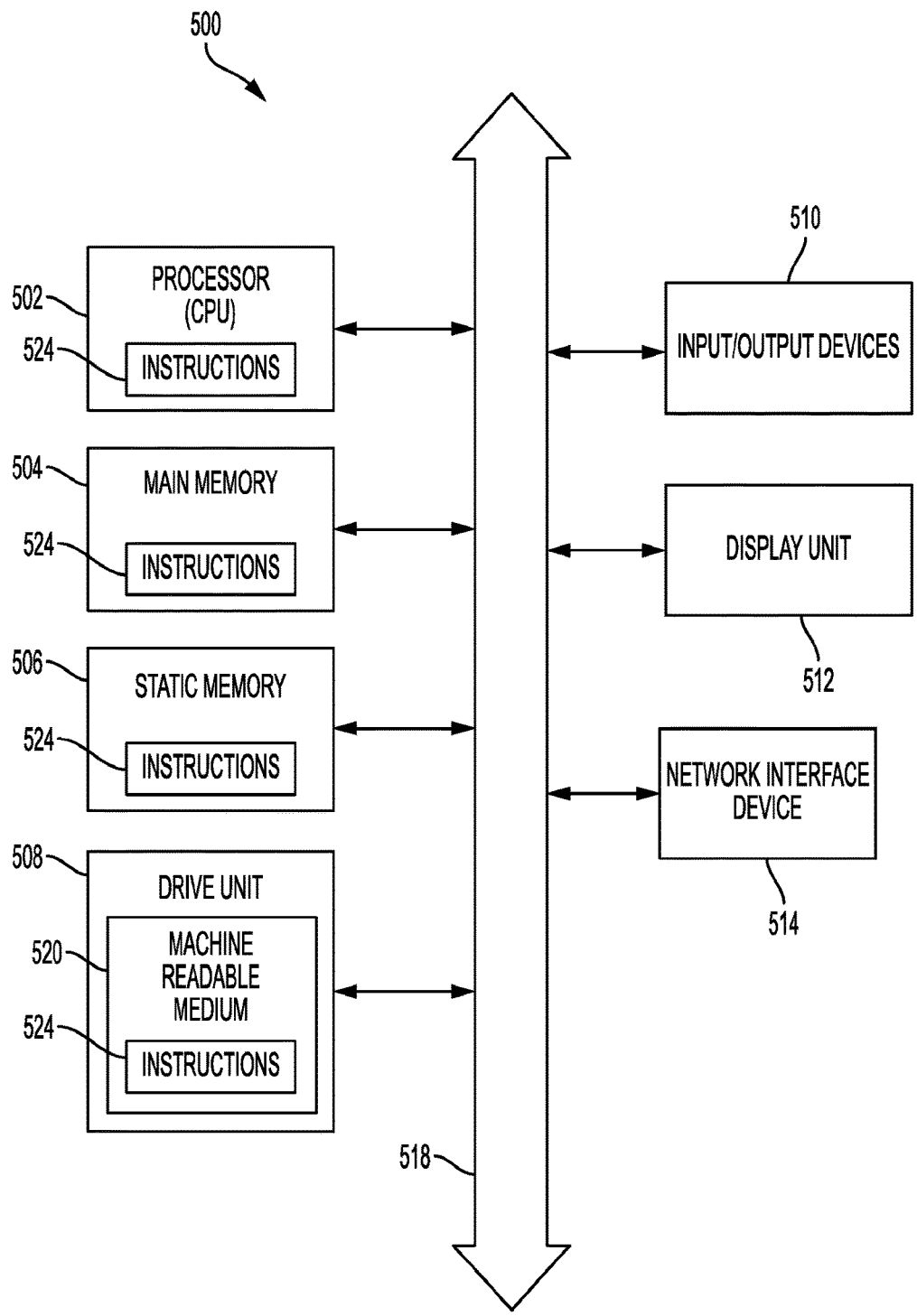
FIG. 5 is a schematic illustration of an exemplary computing device.

Referring now to FIG. 5, there is shown a hardware block diagram comprising an exemplary computer system 500. The machine can include a set of instructions which are used to cause the computer system to perform any one or more of the methodologies discussed herein. In a networked deployment, the machine can function as a server or a router. In one or more scenarios, the exemplary computer system 500 can correspond to the computing system 200 of FIG. 2.

The computer system 500 can operate independently as a standalone device. However, the present solution is not limited in this regard and in other scenarios the computer system can be operatively connected (networked) to other machines in a distributed environment to facilitate certain operations described herein. Accordingly, while only a single machine is illustrated in FIG. 5, it should be understood that the present solution can be taken to involve any collection of machines that individually or jointly execute one or more sets of instructions as described herein.

The computer system 500 is comprised of a processor 502 (e.g., a Central Processing Unit ("CPU")), a main memory 504, a static memory 506, a drive unit 508 for mass data storage and comprised of machine readable media 520, input/output devices 510, a display unit 512 (e.g., a Liquid Crystal Display ("LCD"), a solid state display, or a Cathode Ray Tube ("CRT")), and a network interface device 514. Communications among these various components can be facilitated by means of a data bus 518. One or more sets of instructions 524 can be stored completely or partially in one or more of the main memory 504, static memory 506, and drive unit 508. The instructions can also reside within the processor 502 during execution thereof by the computer system. The input/output devices 510 can include a keyboard, a keypad, a mouse, buttons, a multi-touch surface (e.g., a touchscreen), a speaker, a microphone, an imaging capturing device, and so on. The network interface device 514 can be comprised of hardware components and software or firmware to facilitate wired or wireless network data communications in accordance with a network communication protocol utilized by a data network (e.g., a Local Area Network ("LAN") and/or a Wide Area Network ("WAN")).

The drive unit 508 can comprise a machine readable medium 520 on which is stored one or more sets of instructions 524 (e.g., software) which are used to facilitate one or more of the methodologies and functions described herein. The term "machine-readable medium" shall be understood to include any tangible medium that is capable of storing instructions or data structures which facilitate any one or more of the methodologies of the present disclosure. Exemplary machine-readable media can include magnetic media, solid-state memories, optical-media and so on. More particularly, tangible media as described herein can include; magnetic disks; magneto-optical disks; CD-ROM disks and DVD-ROM disks, semiconductor memory devices, Electrically Erasable Programmable Read-Only Memory ("EEPROM")) and flash memory devices. A tangible medium as described herein is one that is non-transitory insofar as it does not involve a propagating signal.

Computer system 500 should be understood to be one possible example of a computer system which can be used in connection with the various implementations. However, the present solution is not limited in this regard and any other suitable computer system architecture can also be used without limitation. Dedicated hardware implementations including, but not limited to, application-specific integrated circuits, programmable logic arrays, and other hardware devices can likewise be constructed to implement the methods described herein. Applications that can include the apparatus and systems of various implementations broadly include a variety of electronic and computer systems. Some implementations may implement functions in two or more specific interconnected hardware modules or devices with related control and data signals communicated between and through the modules, or as portions of an application-specific integrated circuit. Thus, the exemplary system is applicable to software, firmware, and hardware implementations.

Further, it should be understood that the present solution can take the form of a computer program product on a tangible computer-usable storage medium (for example, a hard disk or a CD-ROM). The computer-usable storage medium can have computer-usable program code embodied in the medium. The term computer program product, as used herein, refers to a device comprised of all the features enabling the implementation of the methods described herein. Computer program, software application, computer software routine, and/or other variants of these terms, in the present context, mean any expression, in any language, code, or notation, of a set of instructions intended to cause a system having an information processing capability to perform a particular function either directly or after either or both of the following: a) conversion to another language, code, or notation; or b) reproduction in a different material form.

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods and sequence of steps of the method without departing from the concept, spirit and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

We claim:

1. A method for non-invasive and non-destructive determinations of mechanical properties of a material, comprising:
coupling a first end of the material to a first mechanical mechanism which is movable in a first direction and coupling a second end of the material to a second mechanical mechanism which is movable in a second direction opposed to the first direction;
applying a first pulling force to the material by moving the first and second mechanical mechanisms a first distance in respective first and second directions;
applying an oscillating force to the material having the first pulling force applied thereto;
applying a second pulling force to the material by moving the first and second mechanical mechanism a second distance in respective first and second directions, where the second pulling force causes any undulations in the material to be removed and causes a loading of fibers or polymeric units that support the material;
allowing the material to oscillate through a series of cycles of loading and unloading;
measuring a strain and stress on the material as a function of time while the material oscillates;
determining a natural frequency of the material based on the strain or stress previously measured; and
determining an elastic modulus of the material using the natural frequency.

2. The method according to claim 1, wherein the material comprises a material used in a commercial process, a material used in a laboratory process, a tissue in a living animal, or a tissue removed from a living animal.

3. The method according to claim 1, wherein the oscillating force is applied to the material by a vibrating hammer, an oscillating hydraulic device, an oscillating acoustic device, an oscillating magnetic field generator, an oscillating electrical field generator, an oscillating electromagnetic field generator, or an oscillating piezoelectric crystal.

4. The method according to claim 1, wherein the oscillating force comprises an oscillating acoustic force.

5. The method according to claim 4, wherein a tension of the material ranges from 0-500 N when the oscillating force is being applied thereto.

6. The method according to claim 1, wherein the material is allowed to oscillate through a series of cycles of loading and unloading at frequencies between 10-2000 Hz.

7. The method according to claim 1, wherein the elastic modulus is determined using the following Mathematical Equation $$E = (2\pi f_n m)^2 \left(\frac{L}{A}\right)$$

where E represents a modulus, $f_n$ is the natural vibration frequency, m represents a mass, L represents a length of the material, and A represents a cross-sectional area.

8. The method according to claim 7, wherein the elastic modulus is obtained by multiplying the modulus E by an elastic fraction measured separately on the material from incremental stress-strain curves.

9. The method according to claim 1, further comprising measuring a viscoelasticity of the material when the oscillating force is being applied to the material.

10. The method according to claim 1, further comprising transforming a first diagnosis into a more precise second diagnosis based on the elastic modulus.

11. A system, comprising:
first and second mechanical mechanisms to which first and second ends of a material are respectively coupled and which
apply a first pulling force to the material by respectively moving in first and second opposing directions a first distance, and
apply a second pulling force to the material by respectively moving in the first and second opposing directions a second distance, where the second pulling force causes any undulations in the material to be removed and causes a loading of fibers or polymeric units that support the material;
an oscillating force generator applying an oscillating force to the material having the first pulling force applied thereto, where the material is allowed to oscillate through a series of cycles of loading and unloading; and
a computing system determining an elastic modulus of the material using a natural frequency of the material that is determined based on a strain and stress measured on the material as a function of time while the material oscillates.

12. The system according to claim 11, wherein the material comprises a material used in a commercial process, a material used in a laboratory process, a tissue in a living animal, or a tissue removed from a living animal.

13. The system according to claim 11, wherein the oscillating force generator is selected from the group consisting of a vibrating hammer, an oscillating hydraulic device, an oscillating acoustic device, an oscillating magnetic field generator, an oscillating electrical field generator, an oscillating electromagnetic field generator, and an oscillating piezoelectric crystal.

14. The system according to claim 11, wherein the oscillating force comprises an oscillating acoustic force.

15. The system according to claim 14, wherein a tension of the material ranges from 0-500 N when the oscillating force is being applied thereto.

16. The system according to claim 11, wherein the material is allowed to oscillate through a series of cycles of loading and unloading at frequencies between 10-2000 Hz.

17. The system according to claim 11, wherein the elastic modulus is determined using the following Mathematical Equation $$E = (2\pi f_n m)^2 \left(\frac{L}{A}\right)$$

where E represents a modulus, $f_n$ is the natural vibration frequency, m represents a mass, L represents a length of the material, and A represents a cross-sectional area.

18. The system according to claim 17, wherein the elastic modulus is obtained by multiplying the modulus E by an elastic fraction measured separately on the material from incremental stress-strain curves.

19. The system according to claim 11, wherein a viscoelasticity of the material is measured when the oscillating force is being applied to the material.

20. The system according to claim 11, wherein the computing system further transforms a first diagnosis into a more precise second diagnosis based on the elastic modulus.

* * * * *